United States Patent
Christoudias

(10) Patent No.: US 7,731,713 B2
(45) Date of Patent: Jun. 8, 2010

(54) VERSATILE IRRIGATION SYSTEM DISSECTOR

(75) Inventor: George C. Christoudias, Teaneck, NJ (US)

(73) Assignee: Surgical Invention & Innovations, Teaneck, NJ (US)

(*) Notice: Subject to any disclaimer, the term of this patent is extended or adjusted under 35 U.S.C. 154(b) by 755 days.

(21) Appl. No.: 11/277,830

(22) Filed: Mar. 29, 2006

(65) Prior Publication Data
US 2007/0233059 A1    Oct. 4, 2007

(51) Int. Cl.
*A61B 18/14* (2006.01)
(52) U.S. Cl. .............................. 606/42; 606/45; 606/49
(58) Field of Classification Search ................... 606/42, 606/45, 49
See application file for complete search history.

(56) References Cited

U.S. PATENT DOCUMENTS

| | | | | |
|---|---|---|---|---|
| 5,348,555 A | * | 9/1994 | Zinnanti | 606/49 |
| 5,609,573 A | * | 3/1997 | Sandock | 604/22 |
| 5,817,121 A | * | 10/1998 | Christoudias | 606/190 |
| 6,391,040 B1 | * | 5/2002 | Christoudias | 606/162 |
| 6,620,161 B2 | * | 9/2003 | Schulze et al. | 606/51 |
| 6,908,463 B2 | * | 6/2005 | Treat et al. | 606/29 |

* cited by examiner

*Primary Examiner*—Lee S Cohen
(74) *Attorney, Agent, or Firm*—Richard A. Joel, ESQ

(57) ABSTRACT

A versatile irrigation system dissector for laparoscopic surgery comprises an elongated lumen having an elongated slim tip electrode slidably mounted therein and having a cutting tip extendable therefrom at one end. The lumen is connected at the other end to a manifold mounted on a handle, which includes a pair of switches to regulate the inlet and outlet flow through the lumen for irrigation and suction purposes. A control panel on the handle regulates the current to the tip for either cutting or coagulating. Thus, several operations may be performed with a single handheld instrument in a highly efficient and rapid action.

13 Claims, 5 Drawing Sheets

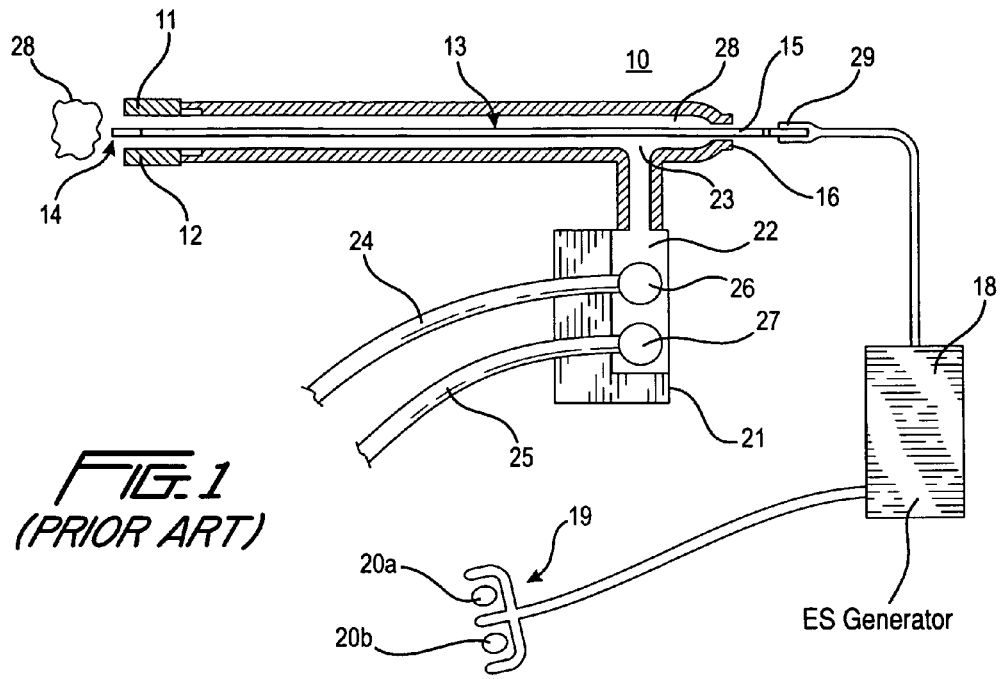
FIG. 1
(PRIOR ART)
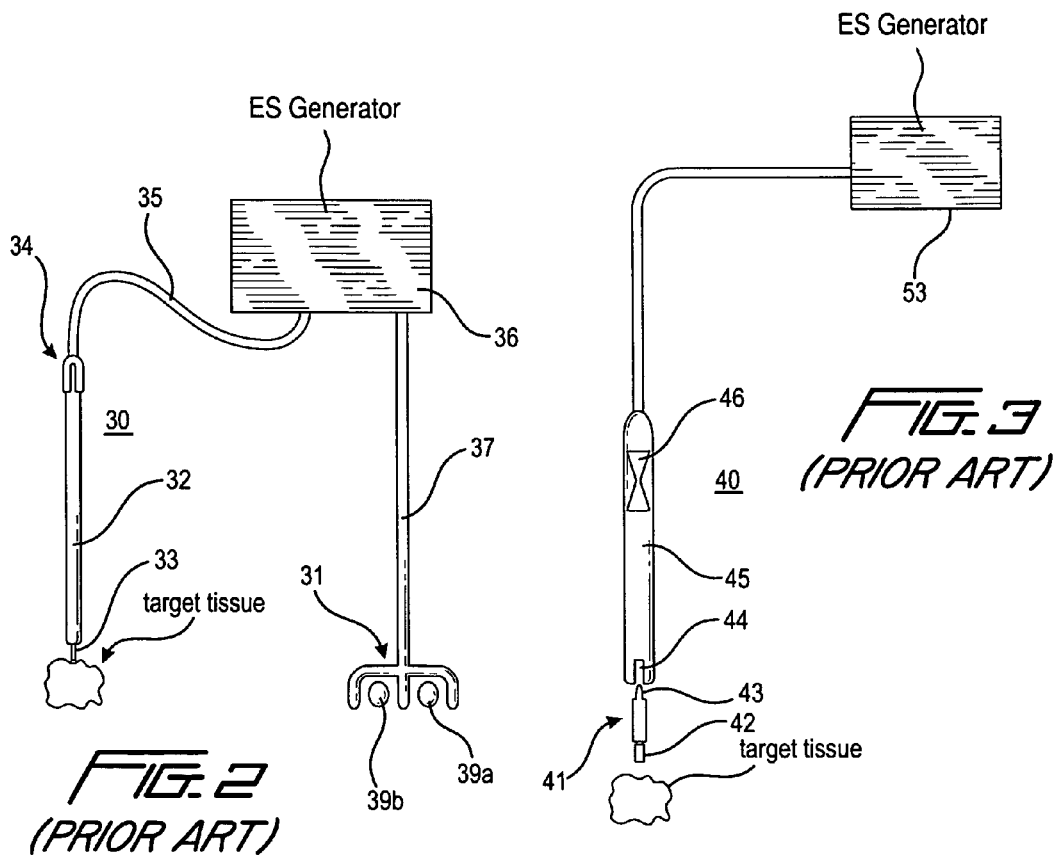
FIG. 2
(PRIOR ART)
FIG. 3
(PRIOR ART)

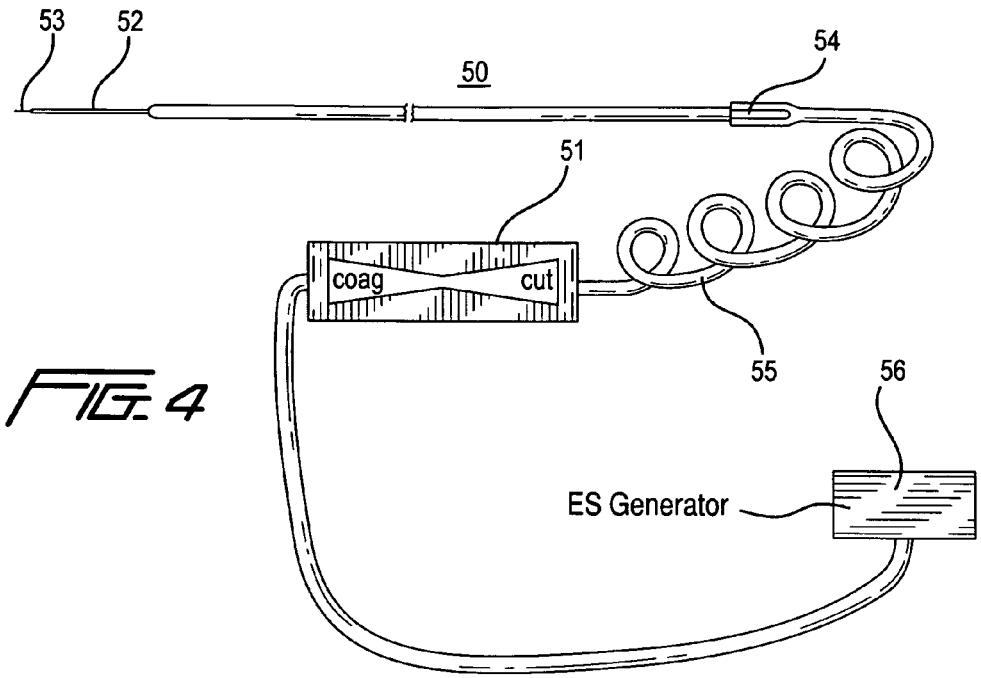
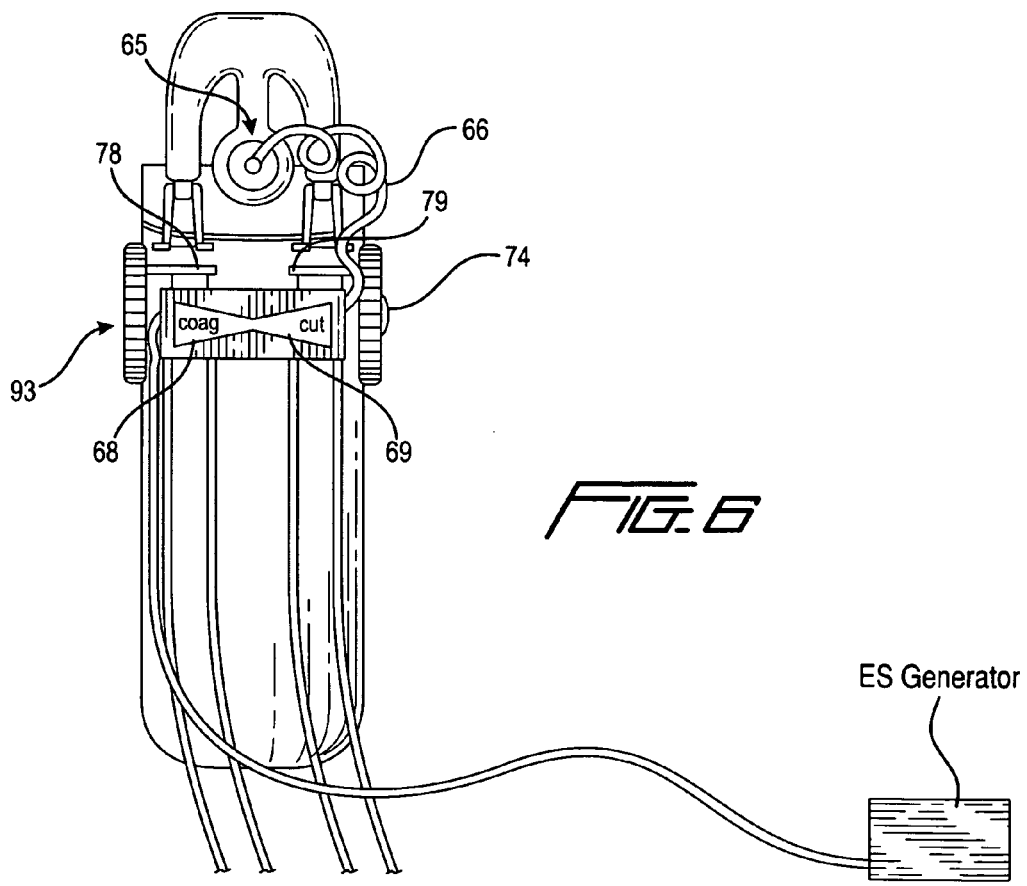

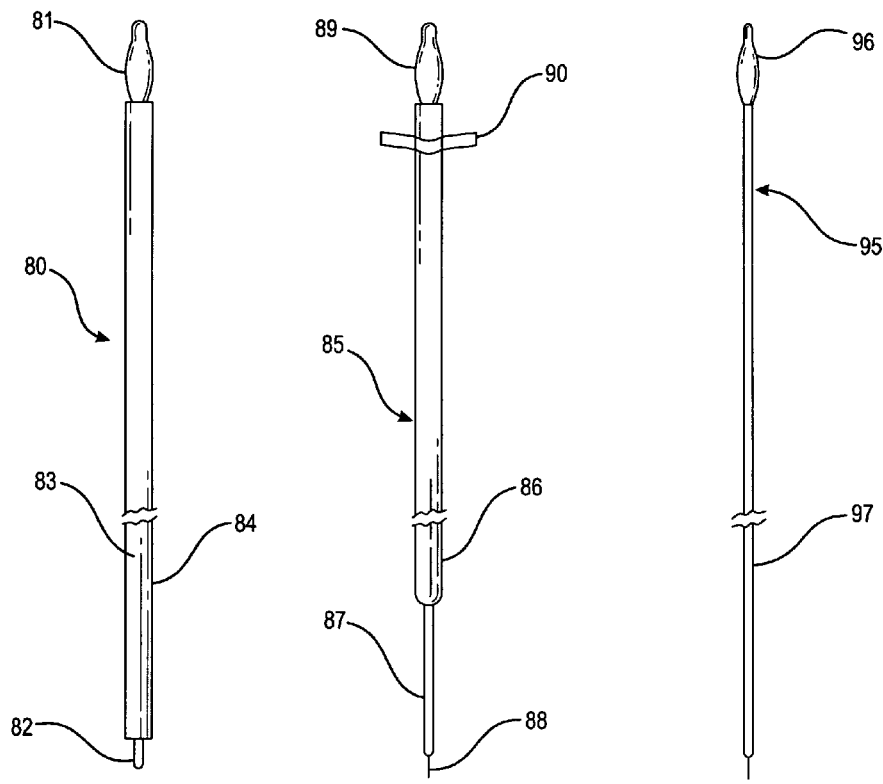
FIG. 7a (PRIOR ART)  FIG. 7b (PRIOR ART)  FIG. 7c (PRIOR ART)
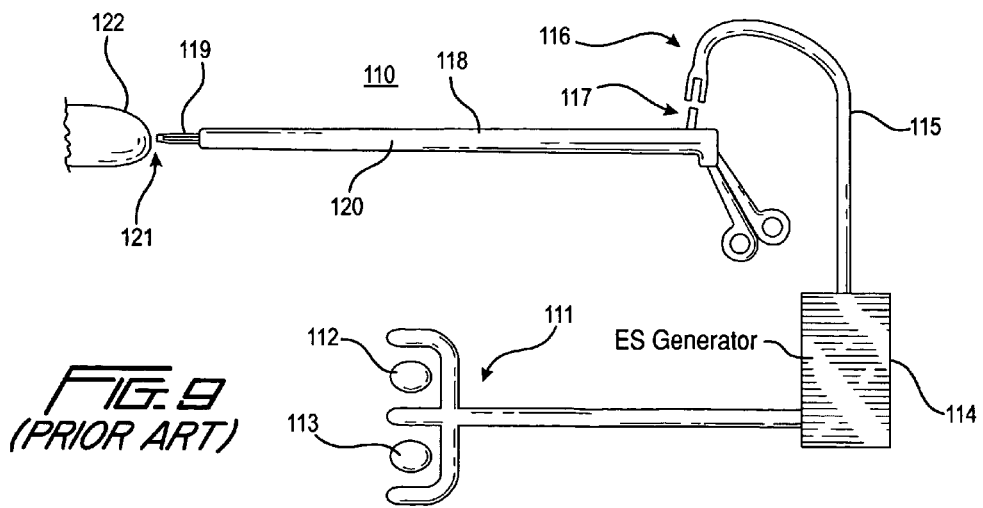
FIG. 9 (PRIOR ART)

US 7,731,713 B2

VERSATILE IRRIGATION SYSTEM DISSECTOR

CROSS REFERENCE TO RELATED APPLICATIONS

Not Applicable

STATEMENT REGARDING FEDERALLY SPONSORED RESEARCH OR DEVELOPMENT

Not Applicable

PARTIES TO A JOINT RESEARCH AGREEMENT

Not Applicable

BACKGROUND OF THE INVENTION

This invention comprises a new and improved instrument for irrigating and dissecting tissue during laparoscopic procedures.

1. Field of the Invention

In the field of laparoscopic surgery, many new instruments have been introduced with the increasing number of procedures and the growing familiarity with the endoscopic modality of operating. The use of such instruments for dissecting is shown in applicant's earlier U.S. Pat. No. 5,817,121, which discloses an endodissector. A more recent instrument by applicant for dissecting is shown in U.S. Pat. No. 6,391,040, which discloses an endodissector with a distinctive tip at the operative end.

2. Description of Related Art Including Information Disclosed Under 37 CFR 1.97 & 1.98

U.S. Pat. No. 6,620,161 to Schulze et al discloses an electrosurgical instrument useful in controlling-coagulating blood vessels such as veins and arteries. The instrument includes a handle assembly with first and second actuators and an elongated tube assembly, which is supplied with current for grasping a dissecting tissue.

U.S. Pat. No. 6,908,463 to Treat et al discloses an electrothermal device for sealing and dividing tissue, which is particularly suitable for laparoscopic and endoscopic surgery.

The prior art, however, fails to disclose the unique instrument of the present invention which is simple to use, highly manipulative and inexpensive. The electrode for dissecting is retractable within a lumen, which also includes concentric space about the electrode for irrigation and suction or alternatively, the electrode could be easily withdrawn within the lumen to facilitate irrigation and suction. A control panel on the handle regulates the current at the tip for either coagulation or cutting. A pair of switches mounted on the handle for the lumen and electrode controls a pair of tube lines coupled to a manifold for irrigating or suction during a procedure. Advantageously, dissecting, irrigation and suction may be performed with a single handheld instrument. Electrocoagulation is operated in conjunction with an electrocoagulation and a suction-irrigation system with a gauze dissector tip.

BRIEF SUMMARY OF THE INVENTION

This invention involves a unique dissector comprising an elongated lumen having an electrode mounted therein and slidable in or out at the working end from the elongated lumen. The other end of the electrode protrudes from the lumen and includes a manipulating protrusion used for gripping and limiting the extension of the electrode from the working end and means coupling the electrode to a power source.

The lumen is connected to a manifold at the non-working end, which has an inlet on one side thereof and an outlet on the other side and is mounted on a handle to manipulate the dissector. An inlet tube is connected to the lumen for irrigation purposes, whereas the other outlet tube is connected to the lumen for suction purposes. Respective switches are mounted to the manifold to control the flow that can be adjusted at variable volumes from the inlet tubing and the outlet tubing. The tubing is connected to the respective manifold openings. The switches each control a projecting pin, which engages and opens or closes the respective tubing as desired, or engages the tubing at variable but stable positions, which alters the flow at different volumes.

To operate, the instrument or cannula is inserted into a body opening and the electrode with a particular slim tip is extended to contact the particular tissue. A switch on the manifold controls the current to the electrode. The electrode is activated for dissection and/or coagulation as desired. The particular switch is then activated for irrigation or suction as indicated or desired. The operations are all conveniently performed with the same handheld instrument with a particular digit such as the thumb.

Accordingly, an object of this invention is to provide a new and improved dissector for use in laparoscopic surgery.

Another object of this invention is to provide a new and improved irrigation system and dissector, which includes a dissecting electrode mounted within an elongated lumen, which is also used for irrigation and suction with the controls for all activities resting within the reach of the activating digit i.e., the thumb.

A further object of this invention is to provide a new and improved dissector, which includes an electrode slidable within a lumen and mounted to a manifold with separate lines under control of respective switches connected to said manifold for purposes of irrigation and suction in a single instrument.

Another object of this invention is to provide a new and improved dissector, which includes control means conveniently located on a manifold to regulate the irrigation and suction action of the lumen as desired during a dissecting procedure and a switch to control current for dissecting and coagulation with a unique slim tip electrode.

A more specific object of this invention is to provide a new and improved handheld dissector having an elongated retractable electrode positioned within a lumen, and suction and irrigation means coupled to the lumen and mounted on a manifold having control means for regulating the current to the electrode and suction-irrigation control means and said controls and mounted on a handle for ease of manipulation.

A further more specific object of this invention is to provide simultaneous electrocoagulation and suction for a smoke free surgical field by allowing simultaneous activation of the electrocoagulation and suction controls.

BRIEF DESCRIPTION OF THE DRAWINGS

The above and other objects and advantages of the present invention may be more clearly seen when viewed in conjunction with the accompanying drawings wherein:

FIG. 1 is a schematic side view of a prior art system showing electrocoagulation operated in conjunction with a suction-irrigation arrangement;

FIG. 2 shows a prior art foot control electrocoagulation system;

FIG. 3 shows a prior art hand-control electrocoagulation system;

FIG. 4 shows a unique slim tip electrode used in conjunction with a suction-irrigation system;

FIG. 6 is a rear view of the handle and controls for the electrode and for the irrigation and suction valves;

FIG. 7a is a side view of a standard electrode while FIG. 7b shows a slim tip electrode and FIG. 7c shows a conventional slim electrode.

DETAILED DESCRIPTION OF THE INVENTION

Figure 5:
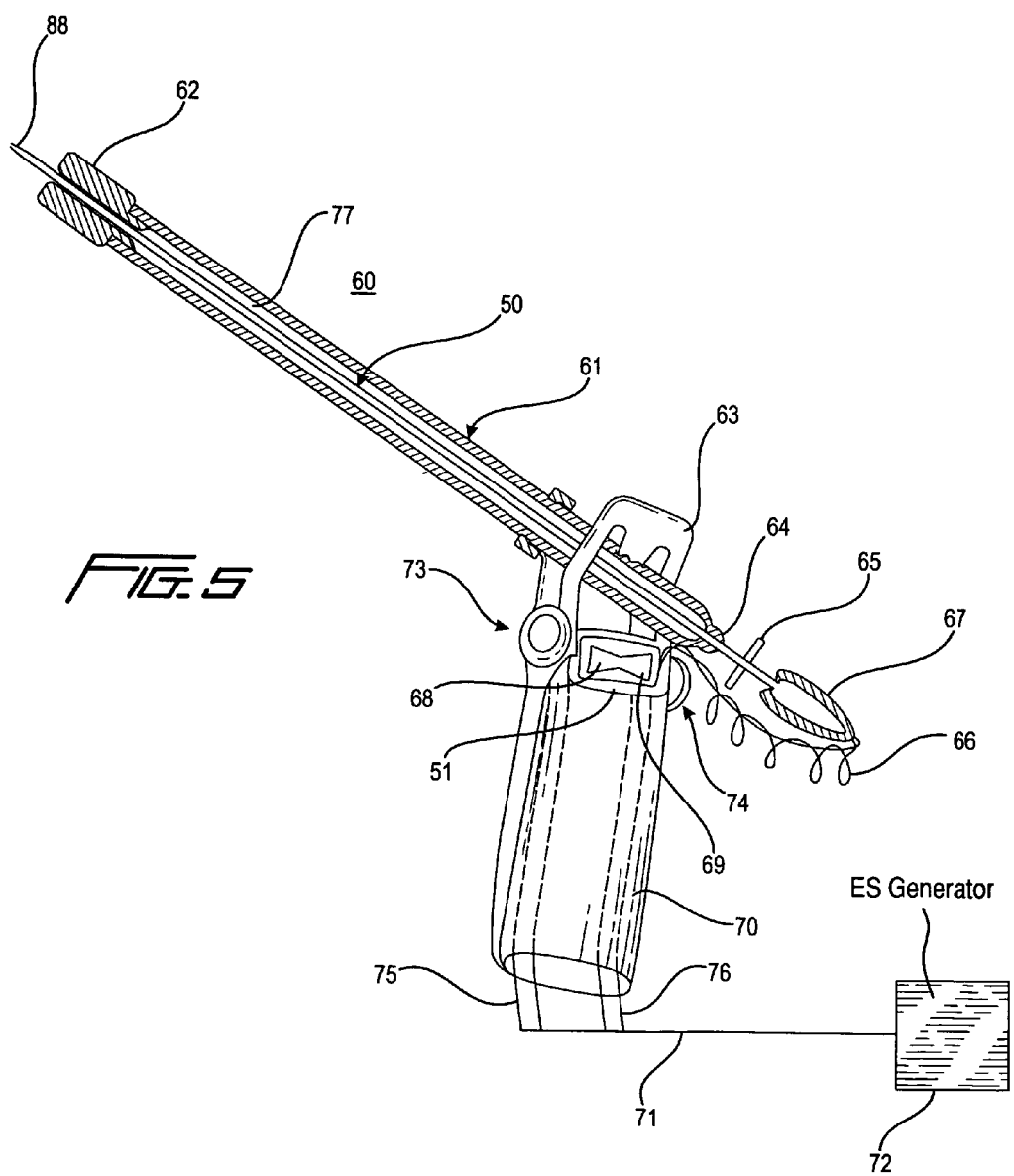
FIG. 5 is a perspective view of a unique versatile irrigation system-dissector using the electrode of FIG. 4.

Referring now to the drawings, FIG. 1 depicts a prior art device 10 for electrocoagulation operated in conjunction with a gauze dissector tip 11 on one end of the cannula 12. The electrode 13 comprises a cutting and coagulating tip 14 extending outwardly from the gauze tip 11 on the cannula 12 to contact target tissue 28. An insulated body portion 15 extends axially along the lumen 28 and protrudes outwardly from the other end 16 thereof. The electrode end with stalk 29 is connected by wire 17 to a power supply 18. A foot control 19 activates the power supply 18 to supply current to the tip 14 for coagulating or cutting. The foot pedal or control 19 has separate switches 20a and 20b for cutting or coagulation.

The cannula 12 is mounted on a handle 21 which includes a hollow chamber 22 connected to a cannula aperture 23. Hoses 24 and 25 for suction and irrigation respectively, are connected to a suction control 26 and an irrigation control 27 to regulate flow.

FIG. 2 shows a prior art device 30 for electrocoagulation using a foot control 31. An electrode 32 having a cutting/coagulating tip 33 at one end is mounted in an electrode receptacle 34. A connecting wire 35 is mounted to the receptacle 34 at one end and to an electrical source or power supply 36 at the other end. A foot control 31 is connected via wire 37 and regulates the power supply 36. The foot control 31 includes pedal 39a to regulate coagulating current and 39b to regulate current for cutting.

FIG. 3 depicts schematically a hand control electrocoagulation device 40 of the prior art. An electrode 41 having a coagulating/cutting tip 42 at one end is mounted at the other end 43 in an electrode receptacle 44 in a pencil like body 45. A switch 46 having a setting for coagulation current control and a setting for cutting current control is mounted on the body 45 and is connected by wire 46 to the electrical source 47. The target tissue 48 is contacted by the tip 42 for either coagulation or cutting as determined by the switch setting.

FIG. 4 shows an electrode 50 used in the embodiment of the invention shown in FIG. 5. The slim tip electrode 50 is used in conjunction with a suction/irrigation device with a hand control panel 51 mounted on the control handle of the device. The 1.5 mm slim tip 52 allows passage through the 5 mm end of a dissector's lumen and terminates in an exposed coagulating-cutting tip 53. The electrode 50 includes an electrode-connecting stalk 54 at the other end, a wire 55 joining the control panel 51 to said stalk 54 and a wire 57 joining the panel 51 to a power source 56.

FIG. 5 shows the versatile irrigation system dissector 60 of this invention. The electrode 50 of FIG. 4 is mounted within the irrigation cannula 61, which may be 5 mm or 10 mm in diameter. A gauze dissector 62 for blunt dissection is mounted on one end of the cannula 61. The cannula 61 is mounted to a manifold 63 adjacent its other end 64 through which the electrode 50 extends. An electrode manipulation disc 65 is mounted about the electrode for movement within the cannula 61. The end of the electrode 50 is connected to a coiled wire 66 via coupling 67. The wire 66 connects to control panel 51, which includes switches 68 and 69, which regulate the current for either electrocoagulation or cutting. The panel 51 is mounted to the handle 70 of the suction irrigation device for hand-controlled electrocoagulation. The control panel 51 is connected by wire 71 to a generator 72.

The manifold 63 includes a suction valve 73 on one side of the handle 70 and an irrigation valve 74 on the other side of the handle 70. The valves 73 and 74 are connected to the respective hoses 75 and 76 to control suction and irrigation through the manifold 63 and lumen 77. Thus, the versatile irrigating system dissector 60 includes all the controls on a handle 70 for hand operation of the electrode 50 and irrigation and suction using the cannula lumen 77.

FIG. 6 shows the handle controls in greater detail. The electrode manipulation device 65 is connected by a coiled wire 66 to the control panel 51. The panel includes centrally pivotal switches 68 for coagulation and 69 for cutting. The switches 68 and 69 are connected as shown to power supply and regulate the current supplied to the tip 88. The suction control valve 73 includes a pin 78, which presses against the flexible suction tubing 75 to regulate suction. Similarly, control valve 74 includes a pin 79, which engages flexible irrigation tube 79 to control the flow therethrough.

FIG. 7a depicts a standard 3-5 mm OD electrode 80 with a connecting stalk 81 at one end and coagulating tip 82 at the other end. The main body portion 83 is covered with a sheath of insulation 84.

FIG. 7b shows a unique slim tip electrode 85 used in this invention. The elongated main shaft 86 is 3 mm in OD thereby helping to maintain the stability of the instrument in lengths necessary for use in laparoscopic surgery. At one end, a slim tip 87 approximately 1.5 mm OD extends 4 cm in length from the insulated shaft 86. At the very end of the slim tip portion 87 is an exposed coagulating tip 88. At the other end of the electrode 85 is a connecting stalk 89 and spaced inwardly therefrom is a manipulator disc 90 mounted about the shaft 86 for insertion or withdrawal of the electrode 85 from the cannula shown in FIG. 5. The slim tip 87 will fit through a 5 mm Christoudias endodissector mentioned in the discussion of the prior art.

FIG. 7c discloses a standard 15 mm electrode 95 wherein the thin shaft 97 renders the electrode 95 flexible and unstable in lengths necessary for laparoscopic surgery. The slim tip electrode 85 eliminates this problem. The electrode 95 also includes a connecting stalk 95 at one end and an exposed coagulating tip 97 at the other end.

Figure 8A:
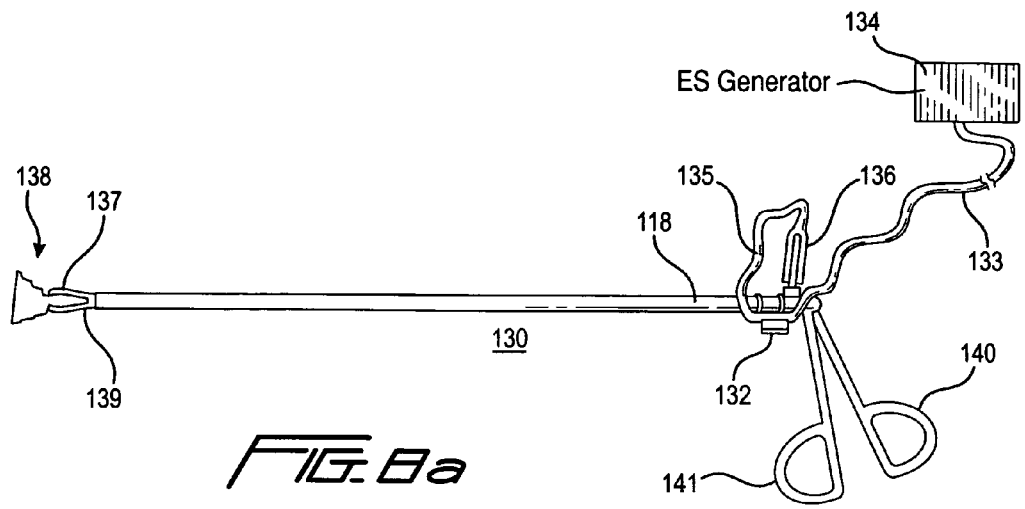
FIG. 8a represents an alternate embodiment of the invention involving a coagulation system and FIG. 8B shows the electrical control panel for the system of FIG. 8a; and, FIG. 9 shows a prior art version of a coagulation system.
Figure 8B:
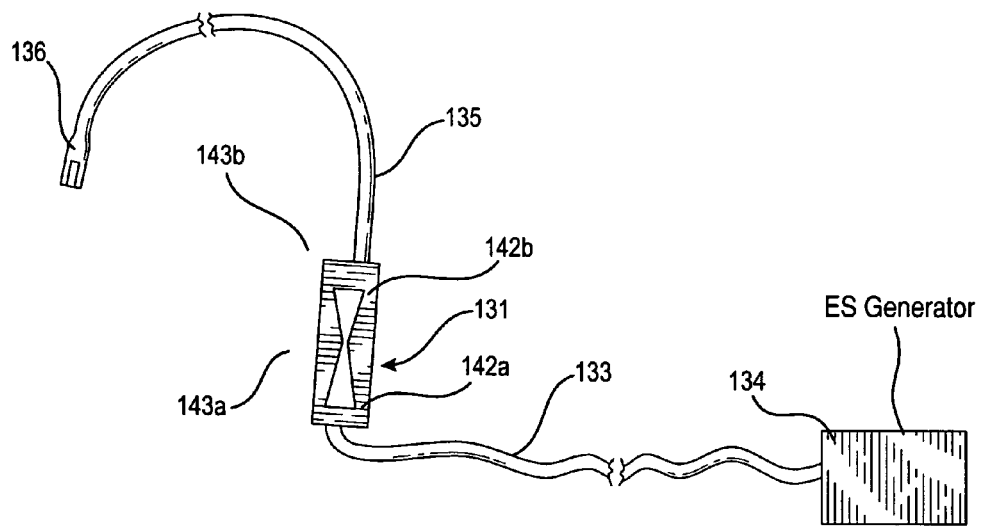

FIGS. 8a and 8b disclose a handheld coagulation system 130 with a control panel 131 mounted on the instrument body 118. The control panel 131 is connected via wire 133 to the electrical source 134. A wire 135 connects the control panel 131 to the electrode connector receptacle 136. Electrode jaws 137 extend outwardly from the tube 132 to engage the target tissue 138 for cutting and coagulation. The insulated electrode 139 protrudes from tube 132 and is actuated by finger loop 140, which moves the jaws 138 into engagement. Loop 141 serves as a gripping loop in the completely handheld coagulation system 130.

FIG. 8b shows the control panel 131 in greater detail with switches 142a and 142b mounted thereon for cutting and coagulating respectively. Straps 143a and 143b are provided for attaching the panel 131 to the instrument body 132. The electrical supply 134 provides current through the control panel 131 to the electrode connector and the electrode 139.

FIG. 9 shows a prior art coagulation system 110 with a foot pedal 111 having a cutting switch 113 coupled to a power source 114. A connecting wire 115 is connected to the power source 114 at one end and to an electrode instrument receptacle 116 at the other end where it engages a connecting tip 117 on the instrument body 118. An electrode 119 extends through on elongated through an elongated supporting tube 120. Electrode instrument jaws 121 extend from one side of the tube 120 to engage the target tissue 122. Pivotal finger grip 123 controls the jaws 121 while finger grip 124 is chiefly for gripping purposes.

While the invention has been explained by a detailed description of certain specific embodiments, it is understood that various modifications and substitutions can be made in any of them within the scope of the appended claims that are intended also to include equivalents of such embodiments.

What is claimed is:

1. A versatile irrigating system dissector comprises:
   a cannula having an elongated body including an aperture at each end portion and including an irrigation channel extending therealong, said end portions including a first cutting end portion and an opposite end connecting portion;
   a manifold having the cannula coupled thereto;
   a first irrigation tube and a second suction tube connected to the manifold at one end;
   an irrigation valve and a suction valve connected to the respective tubes to regulate the flow to the manifold and means for providing fluid to the irrigation tube and means for receiving fluid from the suction tube;
   an electrode slidably mounted within the cannula channel and having a first cutting end portion and an opposite end connecting portion both extending outwardly from the cannula apertures;
   a handle having the manifold and suction and irrigation valves mounted thereto;
   a power supply;
   a control panel mounted on the handle and coupled to the opposite end connecting portion of the electrode at one end and to said power supply at the other end; and,
   wherein the control panel regulates the current to the electrode for cutting or alternatively for coagulation.

2. A dissector in accordance with claim 1 wherein:
   the cannula includes a gauze dissector mounted about the cutting end portion of the electrode thereof.

3. A dissector in accordance with claim 2 wherein:
   the electrode is a slim tip electrode having a main body portion of a predetermined diameter, a reduced diameter portion extending outwardly from the cannula for a predetermined distance at the cutting end portion and a coagulating tip mounted to the reduced diameter portion and extending outwardly therefrom at the end thereof.

4. A dissector in accordance with claim 3 wherein:
   the electrode includes an electrode manipulating disc mounted thereabout adjacent the end connecting portion of the electrode and a connecting stalk at the end connecting portion thereof and a wire connected thereto.

5. A dissector in accordance with claim 4 wherein:
   the control panel includes a pivotal switch for providing current to the tip electrode by the position thereof; and
   said wire comprises a coiled wire having a first end and a second end, a connector at the first end engaging the electrode stalk and being connected to the control panel at the other end.

6. A dissector in accordance with claim 1 wherein:
   the manifold comprises a transverse tube having an intermediate tube coupled thereto and extending downwardly therefrom and a first end tube coupled to the transverse tube and extending downwardly on one side of the intermediate tube and a second end tube coupled to the transverse tube and extending downwardly on the other side of the intermediate tube; and
   the cannula channel being coupled to the intermediate tube.

7. A dissector in accordance with claim 1 including:
   a manipulating disc mounted to the electrode and extending outwardly therefrom wherein
   the electrode is slidable within the cannula channel by movement of the manipulating disc.

8. A dissector in accordance with claim 1 wherein:
   the suction tube and the irrigation tube are flexible tubes.

9. A dissector in accordance with claim 8 wherein:
   the handle includes opposite sides; and,
   the irrigation valve and the suction valve each comprise rotatable circular members, the suction valve and irrigation valve being mounted on the opposite sides of the handle, and each rotatable valve member includes a pin extending inwardly to engage the respective suction and irrigation tubes and regulate the flow therethrough.

10. A dissector in accordance with claim 9 wherein:
    the suction valve can be rested at a desired flow position while the control is activated for electrocoagulation causing aspiration of the smoke from the coagulation as it is produced and effecting a clean, smoke free, surgical field.

11. A dissector in accordance with claim 1 wherein:
    the electrode includes a first cutting end and a second connecting end and further comprises a main body portion of sufficient diameter to maintain the stability of the electrode, said portion having an insulation sheet thereabout, a connecting stalk at one end of the electrode and a manipulation disc mounted thereabout at a predetermined distance from said second end, and a slim tip extending therefrom at the first cutting end forming an exposed coagulating tip at the termination thereof.

12. A dissector in accordance with claim 11 wherein:
    the main body portion has an OD of approximately 2.7-3 mm and the slim tip has an OD of approximately 1.5 mm.

13. A dissector in accordance with claim 11 wherein:
    the slim tip is approximately 4.25 cm in length.

* * * * *